(12) United States Patent
Van Dyk et al.

(10) Patent No.: US 9,587,135 B2
(45) Date of Patent: Mar. 7, 2017

(54) AQUEOUS DISPERSION OF COMPOSITE PARTICLES

(71) Applicants: Rohm and Haas Company, Philadelphia, PA (US); Dow Global Technologies LLC, Midland, MI (US)

(72) Inventors: Antony K. Van Dyk, Blue Bell, PA (US); Jonathan P. DeRocher, Coopersburg, PA (US); Kevin J. Henderson, Phoenixville, PA (US); Lidaris San Miguel Rivera, Midland, MI (US); Anurima Singh, Audubon, PA (US)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/868,891

(22) Filed: Sep. 29, 2015

(65) Prior Publication Data

US 2016/0090502 A1    Mar. 31, 2016

Related U.S. Application Data

(60) Provisional application No. 62/057,330, filed on Sep. 30, 2014.

(51) Int. Cl.
| | | |
|---|---|---|
| *C09D 133/14* | (2006.01) | |
| *C08F 220/06* | (2006.01) | |
| *C08F 220/14* | (2006.01) | |
| *C08F 220/34* | (2006.01) | |
| *C09D 5/00* | (2006.01) | |
| *C09C 1/36* | (2006.01) | |
| *C09D 5/02* | (2006.01) | |
| *C08F 222/14* | (2006.01) | |
| *C09D 7/12* | (2006.01) | |
| *C08F 283/01* | (2006.01) | |
| *C09D 17/00* | (2006.01) | |
| *C09D 133/08* | (2006.01) | |
| *A61Q 17/04* | (2006.01) | |
| *A61K 8/81* | (2006.01) | |
| *A61K 8/04* | (2006.01) | |
| *C08K 3/22* | (2006.01) | |

(52) U.S. Cl.
CPC .............. *C09D 133/14* (2013.01); *A61K 8/04* (2013.01); *A61K 8/8117* (2013.01); *A61Q 17/04* (2013.01); *C08F 220/06* (2013.01); *C08F 220/14* (2013.01); *C08F 220/34* (2013.01); *C08F 222/14* (2013.01); *C08F 283/01* (2013.01); *C09C 1/3676* (2013.01); *C09D 5/028* (2013.01); *C09D 7/1216* (2013.01); *C09D 17/008* (2013.01); *C09D 133/08* (2013.01); *C08K 3/22* (2013.01); *C08K 2003/2241* (2013.01)

(58) Field of Classification Search
CPC .... C09D 133/14; C09D 133/08; C09D 5/028; C09D 7/1216; C09D 17/008; C09C 1/3676; C08F 220/06; C08F 220/14; C08F 220/34; C08F 222/14; C08F 283/01; C08K 3/22; C08K 2203/2241; A61Q 17/04; A61K 8/8117; A61K 8/04
USPC ......................................................... 524/555
See application file for complete search history.

(56) References Cited

U.S. PATENT DOCUMENTS

| | | | |
|---|---|---|---|
| 7,939,572 B2 * | 5/2011 | Bardman | C08F 2/22 521/134 |
| 2004/0250735 A1 | 12/2004 | McIntyre et al. | |
| 2009/0143540 A1 * | 6/2009 | Ghosh | C09D 133/12 525/417 |

FOREIGN PATENT DOCUMENTS

| | | | | |
|---|---|---|---|---|
| EP | 2692752 A1 * | 2/2014 | | C09D 141/00 |
| EP | 2692753 A1 | 2/2014 | | |
| GB | 1049100 A | 11/1966 | | |
| WO | 2012166691 A1 | 12/2012 | | |

* cited by examiner

*Primary Examiner* — Michael M Bernshteyn
(74) *Attorney, Agent, or Firm* — Karl E. Stauss; Ronald D. Bakule

(57) ABSTRACT

A stable aqueous dispersion including certain composite particles and a method for forming the stable aqueous dispersion is provided. The composite particles include a pigment particle, the pigment particle having disposed thereon a certain water-soluble polymer including copolymerized carboxylic acid monomer and N-containing monomer and the pigment particle bearing the water-soluble polymer having disposed on it a plurality of water-insoluble polymer particles. Also provided is a dry coating formed from the aqueous dispersion.

10 Claims, No Drawings

AQUEOUS DISPERSION OF COMPOSITE PARTICLES

This invention relates to a stable aqueous dispersion including certain composite particles and a method for forming the stable aqueous dispersion. In particular, the invention relates to a composite particle including: a pigment particle, the pigment particle having disposed thereon a water-soluble polymer, the water-soluble polymer comprising, as copolymerized units, from 10% to 30%, by weight based on the weight of the water-soluble polymer, ethylenically unsaturated carboxylic acid monomer when the ethylenically unsaturated carboxylic acid monomer has a molecular weight of from 70 to 100 or from 15% to 40%, by weight based on the weight of the water-soluble polymer, ethylenically unsaturated carboxylic acid monomer when the ethylenically unsaturated carboxylic acid monomer has a molecular weight of from greater than 100 to 500; and from 5% to 95%, by weight based on the weight of said water-soluble polymer, ethylenically unsaturated N-containing monomer selected from the group consisting of Structure I

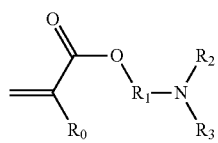

wherein $R_0$ is H, $CH_3$, or $CH_2CH_3$; $R_1$ is $CH_2CH_2$, $CH_2CH(CH_3)$, or $CH_2CH_2CH_2$, or $CH(CH_3)CH_2CH_2$, $CH_2CH_2CH_2CH_2$, $CH(CH_2CH_3)CH_2$, $CH(CH_3)CH(CH_3)$; $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues thereof;

Structure II

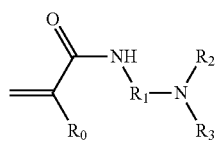

wherein $R_0$ is H, $CH_3$, $CH_2CH_3$; and R1 is $CH_2CH_2$, $CH_2CH(CH_3)$, or $CH_2CH_2CH_2$; $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues thereof;

Structures III - vinyl pyridine

IIIa

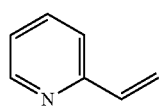

IIIb

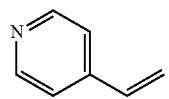

IIIc

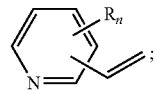

wherein R is $C_1$-$C_4$ alkyl and n is 0 to 4;

Structure IV

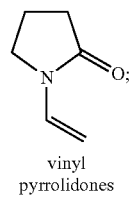

vinyl pyrrolidones and mixtures thereof; wherein the molar ratio of carboxylic acid to N-functionality is from 0.1 to 4; and from 0% to 50%, by weight based on the weight of the water-soluble polymer, (meth)acrylic ester of a linear or branched monohydroxyl or amide of a monoamine compound having from 1 to 4 carbon atoms; or vinyl ester of a linear, branched, cyclic, or aromatic monocarboxylic acid having from 1 to 9 carbon atoms; and wherein the calculated $M_n$ of the water-soluble polymer is from 1,000 to 25,000; and the pigment particle bearing said water-soluble polymer having disposed thereon a plurality of water-insoluble polymer particles in an amount of from 5 to 50% by weight, based on the weight of the composite particles. The invention also relates to a dry coating formed from the aqueous dispersion.

Pigment particles, including as they are known in the coatings art, opacifying pigments, extenders, and particulate colorants provide numerous beneficial properties to dry coatings. Opacifying pigments are particularly important as they provide whiteness and opacity or "hiding" to dry coatings, commonly referred to as paints. Opacifying pigments are present in most coatings that are designed to provide an opaque coating to cover a substrate surface, or a prior applied coating, to which the coating is applied. Pigment particles and mixtures of various pigments may be present whether the dry coating is white or colored. It is desirable that opacifying coatings have a high opacifying efficiency so as to enable the coating to completely conceal the undersurface, even if it is of a sharply contrasting color, while utilizing a minimal thickness of the coating.

Opacifying coating manufacturers have long sought to formulate coatings having a desired opacity by maximizing the level of hiding while minimizing the amount of opacifying pigment utilized. One method to achieve this is to form composite particles with the pigment bearing a plurality of attached or associated water-insoluble polymer particles.

US Patent Application Publication No. 2004/0250735 discloses a process for preparing conditioned titanium dioxide pigments comprising admixing a crude titanium dioxide pigment material, one or more of certain copolymer dispersants, and isolating the conditioned pigment as a dry powder.

WO 2012/166691 discloses an aqueous composition comprising a rheology modifier, titanium dioxide particles, a latex binder, and a composition comprising an amphoteric polymer having pendant acid groups, or salts thereof, and certain pendant mono- or dialkylamino ethylene oxide groups. Sulfonic acid based compositions are preferred. However, in some applications, it is desirable to minimize sulfonate, phosphate, and other strong acid salts as these may cause reduced water resistance and corrosion resistance properties. Polyacrylic acid and polymethacrylic acid homopolymers, copolymers, and related commercial dispersants do not effectively promote the robust formation of latex-pigment composite particles that perform well with certain thickener classes and may lead to poor color acceptance and reduced opacity in certain coatings. We have surprisingly found that certain copolymers of carboxylic acids with certain amine monomers, and an optional third nonionic monomer such as, for example, methyl methacrylate, provide stable, low viscosity, low foam dispersions of various pigments and effectively promote composite particle formation and stable composite dispersions. Composite particles including an opacifying pigment particle such as $TiO_2$, for example, are found to be particularly efficient in contributing to the hiding or opacity of dry coatings. Composite particles including extenders, particulate colorants, and mixtures thereof are expected to provide other improved dry coatings properties as well.

According to a first aspect of the present invention there is provided a stable aqueous dispersion comprising composite particles, said composite particles comprising; a pigment particle, said pigment particle having disposed thereon a water-soluble polymer, said water-soluble polymer comprising, as copolymerized units, from 10% to 30%, by weight based on the weight of said water-soluble polymer, ethylenically unsaturated carboxylic acid monomer when said ethylenically unsaturated carboxylic acid monomer has a molecular weight of from 70 to 100 or from 15% to 40%, by weight based on the weight of said water-soluble polymer, ethylenically unsaturated carboxylic acid monomer when said ethylenically unsaturated carboxylic acid monomer has a molecular weight of from greater than 100 to 500; and from 5% to 95%, by weight based on the weight of said water-soluble polymer, ethylenically unsaturated N-containing monomer selected from the group consisting of Structure I

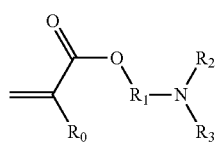

wherein $R_0$ is H, $CH_3$, or $CH_2CH_3$; $R_1$ is $CH_2CH_2$, $CH_2CH(CH_3)$, or $CH_2CH_2CH_2$, or $CH(CH_3)CH_2CH_2$, $CH_2CH_2CH_2CH_2$, $CH(CH_2CH_3)CH_2$, $CH(CH_3)CH(CH_3)$; $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues thereof;

Structure II

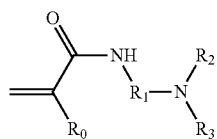

wherein $R_0$ is H, $CH_3$, $CH_2CH_3$; and $R_1$ is $CH_2CH_2$, $CH_2CH(CH_3)$, or $CH_2CH_2CH_2$; $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues thereof;

Structures III - vinyl pyridine

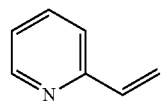
IIIa

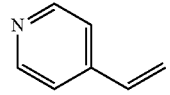
IIIb

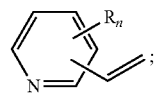
IIIc wherein R is $C_1$-$C_4$ alkyl and n is 0 to 4;

Structure IV

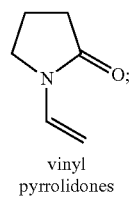

vinyl pyrrolidones and mixtures thereof; wherein the molar ratio of carboxylic acid to N-functionality is from 0.1 to 4; and from 0% to 50%, by weight based on the weight of said water-soluble polymer, (meth)acrylic ester of a linear or branched monohydroxyl or amide of a monoamine compound having from 1 to 4 carbon atoms; or vinyl ester of a linear, branched, cyclic, or aromatic monocarboxylic acid having from 1 to 9 carbon atoms; and wherein the calculated $M_n$ of said water-soluble polymer is from 1,000 to 25,000; and said pigment particle bearing said water-soluble polymer having disposed thereon a plurality of water-insoluble polymer particles in an amount of from 5% to 50% by weight, based on the weight of the composite particles.

According to a second aspect of the present invention there is provided a method for forming a stable aqueous dispersion comprising composite particles comprising: (a) dispersing a pigment particle in an aqueous medium in the presence of from 0.1% to 20%, by weight based on the weight of pigment, of a water-soluble polymer, a water-soluble polymer, said water-soluble polymer comprising, as copolymerized units, from 10% to 30%, by weight based on the weight of said water-soluble polymer, ethylenically unsaturated carboxylic acid monomer when said ethylenically unsaturated carboxylic acid monomer has a molecular weight of from 70 to 100 or from 15% to 40%, by weight based on the weight of said water-soluble polymer, ethylenically unsaturated carboxylic acid monomer when said ethylenically unsaturated carboxylic acid monomer has a molecular weight of from greater than 100 to 500; and from 5% to 95%, by weight based on the weight of said water-soluble polymer, ethylenically unsaturated N-containing monomer selected from the group consisting of:

Structure I

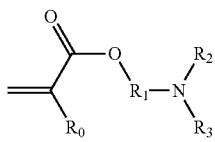

wherein $R_0$ is H, $CH_3$, or $CH_2CH_3$; $R_1$ is $CH_2CH_2$, $CH_2CH(CH_3)$, or $CH_2CH_2CH_2$, or $CH(CH_3)CH_2CH_2$, $CH_2CH_2CH_2CH_2$, $CH(CH_2CH_3)CH_2$, $CH(CH_3)CH(CH_3)$; $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues thereof;

Structure II

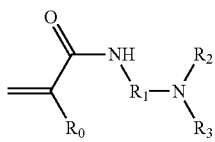

wherein $R_0$ is H, $CH_3$, $CH_2CH_3$; and $R_1$ is $CH_2CH_2$, $CH_2CH(CH_3)$, or $CH_2CH_2CH_2$; $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues thereof;

Structures III - vinyl pyridine

IIIa
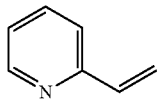

IIIb
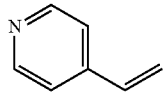

IIIc
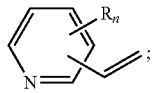

wherein R is $C_1$-$C_4$ alkyl and n is 0 to 4;

Structure IV

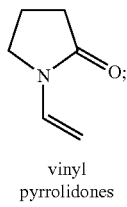

vinyl pyrrolidones and mixtures thereof; wherein the molar ratio of carboxylic acid to N-functionality is from 0.1 to 4; and from 0% to 50%, by weight based on the weight of said water-soluble polymer, (meth)acrylic ester of a linear or branched monohydroxyl or amide of a monoamine compound having from 1 to 4 carbon atoms; or vinyl ester of a linear, branched, cyclic, or aromatic monocarboxylic acid having from 1 to 9 carbon atoms; and wherein the calculated $M_n$ of said water-soluble polymer is from 1,000 to 25,000; and (b) contacting said dispersed pigment particle with an aqueous dispersion of water-insoluble polymer particles in an amount of from 5% to 300% by weight, based on the weight of the composite particles.

According to a third aspect of the present invention there is provided a dry coating formed by the method comprising: forming an aqueous coating composition comprising the stable aqueous dispersion of the first aspect of the present invention; applying said aqueous coating composition to a substrate; and drying, or allowing to dry, said aqueous coating composition.

The present invention relates to a stable aqueous dispersion including composite particles. By "aqueous (medium)" herein is meant water and from 0 to 30%, by wt. based on the weight of the aqueous medium, of water-miscible compound(s). By a "stable aqueous dispersion" herein is meant an aqueous dispersion that passes the heat age stability test detailed in the Experimental Methods herein. By "composite particles" herein is meant particles including at least one water-insoluble pigment particle, a certain water-soluble polymer and a plurality of water-insoluble polymeric particles.

In one embodiment the stable aqueous dispersion is free from strong acid-functional species. By "free from strong acid-functional species" herein is meant that no or a de minimus amount of organic compounds, monomers, copolymerized monomers, polymers and the like, explicitly excluding surfactants, having at least one $pK_a$<3, measured in water at 20° C., are present in the stable aqueous dispersion. In such embodiments less than 0.2%, by weight based on the weight of the stable aqueous dispersion, of strong acid-functional species are present.

The composite particles of the present invention include pigment particles. By "pigment particles" herein is meant inorganic solid water-insoluble particles including pigment particles known in the coatings art as, for example, opacifying pigments, extenders, and particulate colorants; pigment particles may also be solid water-insoluble organic colorants. The pigment particles may be inorganic pigment particles, organic pigment particles, or mixtures thereof. The shape of the pigment particles is not important. Suitable shapes for the pigment particles include spherical shapes, such as a regular sphere, an oblate sphere, a prolate sphere, and an irregular sphere; cubic shapes such as a regular cube and a rhombus; plate-like shapes including a flat plate, a concave plate, and a convex plate; and irregular shapes. The pigment particles having spherical shapes typically have average diameters in the range of from 50 nm to 10 microns; pigment particles having nonspherical shapes typically have average diameters, defined as their maximum dimension, of from 50 nm to 10 microns. The average diameters of pigment particles are typically provided by pigment particle suppliers. The composite particles typically include at least one pigment particle, the water-soluble polymer adsorbed on or associated with the pigment surface, and a plurality of polymer particles disposed thereon. Typically a predominant amount of the composite particles include only one pigment particle. Preferably >80%, more preferably >90%, and most preferably >95%, by number, of the composite particles include only one pigment particle. However, structures including more than one pigment particle are also contemplated; in that event the pigment particles may be the same or different.

Of particular interest are inorganic pigment particles that are opacifying pigments. By "opacifying pigment" herein is meant that the particle engenders opacity when subject to light of a certain wavelength, not necessarily visible light. For example certain nanoparticles included herein provide opacity when subject to light of wavelengths lower than the visible range. The opacifying pigment particle has an average particle diameter of from 50 nm to 10 microns, preferably in the range of from 150 nm to 500 nm, and more preferably, in the range of from 200 nm to 350 nm. Pigment particles having nonspherical shapes preferably have average diameters, defined as their maximum dimension, of from 50 nm to 10 microns, more preferably of from 150 nm to 500 nm, and most preferably of from 200 nm to 350 nm. The opacifying pigment particles have an index of refraction [$n_D$ (20° C.)] of from 1.8 to 5.0. The indices of refraction for various materials are listed in *CRC Handbook of Chemistry and Physics*, 80th *Edition*, D. R. Lide, editor, CRC Press, Boca Raton, Fla., 1999, pages 4-139 to 4-146.

Suitable opacifying pigment particles include zinc oxide, antimony oxide, zirconium oxide, chromium oxide, iron oxide, lead oxide, zinc sulfide, lithopone, and forms of titanium dioxide such as anatase and rutile. Preferably, the opacifying pigment particles are selected from titanium dioxide and lead oxide. More preferably, the pigment particles are selected from rutile titanium dioxide and anatase titanium dioxide. Most preferably, the opacifying pigment particles are rutile titanium dioxide. A coating containing two different forms of a material, such as rutile and anatase titanium dioxide, is considered to have two different pigments.

The opacifying pigment particles may have a uniform composition or a heterogeneous composition with two or more phases. Certain heterogeneous pigment particles have an inner core and surrounding shell structure wherein one type of pigment particle forms the core and another type of particle forms the shell. The core and shell heterogeneous pigment particles include core/shell particles having a shell completely or incompletely encapsulating the core; core/shell particles having more than one core; dipolar particles; and particles having multiple domains of one phase on the surface of the other phase. Pigment particles, such as titanium dioxide, may have at least one coating of one or more of silica, alumina, zinc oxide, and zirconia. For example, in certain embodiments titanium dioxide particles suitable for use in coatings of the present invention may have a coating of silica and a coating of alumina.

The pigment particles may be inorganic pigment particles known in the coatings art as extenders. Extender pigment particles have an index of refraction [$n_D$ (20° C.)] of from greater than 1.3 to less than 1.8. Typical extenders include, for example, magnesium silicate, calcium carbonate, aluminosilcates, silica, various clays such as kaolin and delaminated clay, and talc. Composite particles including extender pigments impart desirable properties such as at least one of hardness, lower gloss, adhesion, stain resistance, and blister resistance.

The pigment particles may be inorganic or organic colorant particles. Suitable inorganic colorant particles include, for example, iron oxide pigments such as goethite, lepidocrocite, hematite, maghemite, and magnetite; chromium oxide pigments; cadmium pigments such as cadmium yellow, cadmium red, and cadmium cinnabar; bismuth pigments such as bismuth vanadate and bismuth vanadate molybdate; mixed metal oxide pigments such as cobalt titanate green, chromate and molybdate pigments such as chromium yellow, molybdate red, and molybdate orange; ultramarine pigments; cobalt oxide pigments; nickel antimony titanates; lead chrome; blue iron pigments; carbon black; and metal effect pigments such as aluminum, copper, copper oxide, bronze, stainless steel, nickel, zinc, and brass; and mixtures thereof. Preferred inorganic colorant particles are iron oxide pigments; bismuth pigments; mixed metal oxide pigments; chromate and molybdate pigments; ultramarine pigments; cobalt oxide pigments; nickel antimony titanates; lead chrome; blue iron pigments; carbon black; metal effect pigments; and mixtures thereof.

The pigment particle has disposed thereon a selected water-soluble polymer, the water-soluble polymer including, as copolymerized units, comprising, as copolymerized units, from 10% to 30%, by weight based on the weight of the water-soluble polymer, ethylenically unsaturated carboxylic acid monomer when the ethylenically unsaturated carboxylic acid monomer has a molecular weight of from 70 to 100 or from 15% to 40%, by weight based on the weight of the water-soluble polymer, ethylenically unsaturated carboxylic acid monomer when the ethylenically unsaturated carboxylic acid monomer has a molecular weight of from greater than 100 to 500; and from 5% to 95%, by weight based on the weight of the water-soluble polymer, ethylenically unsaturated N-containing monomer having the structure:

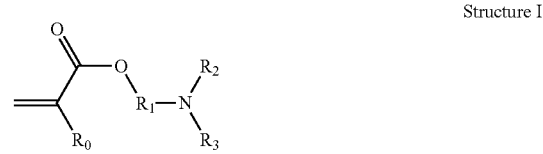

Structure I wherein $R_0$ is H, $CH_3$, or $CH_2CH_3$; $R_1$ is $CH_2CH_2$, $CH_2CH(CH_3)$, or $CH_2CH_2CH_2$, or $CH(CH_3)CH_2CH_2$, $CH_2CH_2CH_2CH_2$, $CH(CH_2CH_3)CH_2$, $CH(CH_3)CH$ ($CH_3$); $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues thereof,

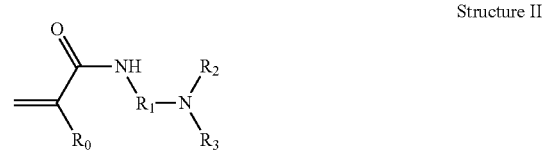

Structure II wherein $R_0$ is H, $CH_3$, $CH_2CH_3$; and $R_1$ is $CH_2CH_2$, $CH_2CH(CH_3)$, or $CH_2CH_2CH_2$; $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues thereof;

Structures III - vinyl pyridines

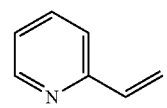

IIIa

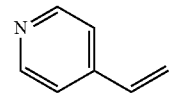

IIIb

-continued

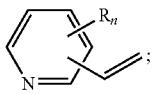
IIIc wherein R is $C_1$-$C_4$ alkyl and n is 0 to 4;

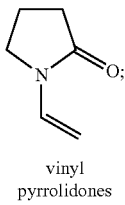
Structure IV vinyl
pyrrolidones and mixtures thereof; wherein the molar ratio of carboxylic acid to N-functionality is from 0.1 to 4; and wherein the calculated $M_n$ of the water-soluble polymer is from 1,000 to 25,000. By "water-soluble" herein is meant that the polymer forms a clear solution in water at pH=8 at 25° C. at greater than 10% w/w, preferably at greater than 20% w/w, and most preferably at greater than 30% w/w. "Carboxylic acid monomer" herein includes, in every instance, salts thereof.

The water-soluble polymer includes, as copolymerized units, comprising, as copolymerized units, from 10% to 30%, by weight based on the weight of the water-soluble polymer, ethylenically unsaturated carboxylic acid monomer when the ethylenically unsaturated carboxylic acid monomer has a molecular weight of from 70 to 100 or, alternatively, from 15% to 40%, by weight based on the weight of the water-soluble polymer, ethylenically unsaturated carboxylic acid monomer when the ethylenically unsaturated carboxylic acid monomer has a molecular weight of from greater than 100 to 500. Ethylenically unsaturated carboxylic acid monomers include, for example, acrylic acid, methacrylic acid, crotonic acid, itaconic acid, fumaric acid, maleic acid, monomethyl itaconate, monomethyl fumarate, monobutyl fumarate, and maleic anhydride. Preferred are (meth)acrylic acid.

The water-soluble polymer also includes, as copolymerized units, from 5% to 95%, preferably from 10% to 50%, by weight based on the weight of the water-soluble polymer, ethylenically unsaturated N-containing monomer selected from the group consisting of Structures I-IV detailed herein above and mixtures thereof. By "$C_3$-$C_{12}$ alkyl groups" herein is meant alkyl groups including saturated, branched, unsaturated cyclic and aromatic groups having the requisite number of carbon atoms. Alternatively, the water-soluble polymer may include, as copolymerized units, the quaternary ammonium analogues of Structure I or Structure II wherein the third alkyl group on the N-atom is selected from $C_1$-$C_{12}$ alkyl groups, preferably methyl or ethyl. Independently, the monomers of Structures III or IV may be ring-substituted as desired.

Examples of the ethylenically unsaturated N-containing monomer include dialkylaminoalkyl acrylates and methacrylates including 2-(N,N-dimethylamino)ethyl methacrylate ("DMAEMA" herein), 2-(N,N-dimethylamino)ethyl acrylate, 2-(N,N-diethylamino)ethyl methacrylate, 2-(N,N-diethylamino)ethyl acrylate 2-(t-butylamino)ethyl methacrylate, 3-(dimethylamino)propyl acrylate, 2-diisopropylaminoethyl methacrylate, and 3-dimethylaminoneopentyl acrylate; dialkylaminoalkyl acrylamides and methacrylamides including N-[2(N,N-dimethylaminoethyl]methacrylamide, N-[3-(N,N-dimethylamino)propyl]acrylamide, and N-[3-(N,N-dimethylamino)propyl]methacrylamide; 2-vinyl pyridine; N-vinyl-2-pyrrolidone; acrylamidotrialkylammonium halides including [2-(acryloxy)ethyl]trimethylammonium chloride, [2-(methacryloxy)ethyl]trimethylammonium chloride, and (3-methacrylamidopropyl)trimethylammonium chloride. Preferred are ethylenically unsaturated N-containing monomers of Structure I. More preferred are dialkylaminoalkyl(meth)acrylates.

The water-soluble polymer may optionally include, as copolymerized units, from 0% to 50%, by weight based on the weight of said water-soluble polymer, (meth)acrylic ester of a linear or branched monohydroxyl or amide of a monoamine compound having from 1 to 4 carbon atoms; or vinyl ester of a linear, branched, cyclic, or aromatic monocarboxylic acid having from 1 to 9 carbon atoms. Examples include methyl(meth)acrylate, ethyl(meth)acrylate, i-propyl (meth)acrylate, n-butyl(meth)acrylate, ethoxyethyl(meth) acrylate, (meth)acrylamide, and vinyl acetate.

Suitable additional optional copolymerized monomers incorporated in the water-soluble polymer, without regard to specific amount, include, as copolymerized units, styrene, butadiene, α-methyl styrene, vinyl toluene, vinyl naphthalene, ethylene, propylene, vinyl chloride, vinylidene chloride, acrylonitrile, (meth)acrylonitrile, various $C_5$-$C_{40}$ alkyl esters of (meth)acrylic acid; such as, for example, 2-ethylhexyl (meth)acrylate, cyclohexyl (meth)acrylate, n-octyl (meth)acrylate, n-decyl (meth)acrylate, n-dodecyl (meth) acrylate, tetradecyl (meth)acrylate, lauryl (meth)acrylate, oleyl (meth)acrylate, palmityl (meth)acrylate, and stearyl (meth)acrylate; other (meth) acrylates such as isobornyl (meth)acrylate, benzyl (meth)acrylate, phenyl (meth)acrylate, 2-bromoethyl (meth)acrylate, 2-phenylethyl (meth) acrylate, and 1-naphthyl (meth)acrylate, higher alkoxyalkyl (meth)acrylates, mono-, di-, trialkyl esters of ethylenically unsaturated di- and tricarboxylic acids and anhydrides, such as ethyl maleate, dimethyl fumarate, trimethyl aconitate, and ethyl methyl itaconate; and hydroxyl-group containing monomers such as hydroxyethyl (meth)acrylate, hydroxypropyl (meth)acrylate, hydroxybutyl (meth)acrylate. As used herein, the term "(meth)acrylate" refers to either acrylate or methacrylate and the term "(meth)acrylic" refers to either acrylic or methacrylic.

In some embodiments the water-soluble polymer is free from strong acid-functional species. By "free from strong acid-functional species" herein with respect to the water-soluble polymer is meant that no or a de minimus amount of copolymerized monomers having at least one $pK_a<3$, measured in water at 20° C., is present in the water-soluble polymer.

In the water-soluble polymer in the present invention the molar ratio of carboxylic acid to N-functionality is from 0.1 to 4, preferably from 0.1 to 0.99. In certain alternative compositions the N-containing monomer is selected from dialkylamino(EO)$_{1-40}$ (meth)acrylates, preferably dibutylamino(EO)$_{1-40}$ (meth)acrylates wherein the molar ratio of carboxylic acid to N-functionality is from 0.1 to 0.99.

In the present invention the "calculated $M_n$" of the water-soluble polymer is from 1,000 to 25,000, preferably from 2,000 to 10,000. "Calculated $M_n$" herein is defined as that determined by the following calculation (The Chemistry of Radical Polymerization, G. Moad and D. Solomon, Elsevier, 2006; Polymer Handbook, J. Brandrup and E. H. Immergut, Wiley, 1989)

$$\frac{1}{DP_n} = C_T \frac{[CTA]}{[M]} + C_I \frac{[I]}{[M]}$$

where $DP_n$ is the degree of polymerization; [M], [CTA], and [I] are the molar amounts of monomer, chain transfer agent, and initiator, respectively; $C_T$ is the CTA transfer efficiency taken as 0.62 herein, and $C_I$ is the initiator efficiency, taken as 0.5 herein. The $M_n$ is calculated as $$M_n = DP_n \times \Sigma m_i [M_i]$$

where $m_i$ is the molar mass of monomer i and $[M_i]$ is the molar fraction of monomer i.

The stable aqueous dispersion of the present invention may further include at least one thickener selected from hydrophobically modified ethoxylated urethanes ("HEUR"), hydroxyethyl cellulose ("HEC"), alkali-soluble emulsions ("ASE"), hydrophobically modified alkali-soluble emulsions ("HASE"), or hydrophobially modified hydroxyethyl cellulose ("HMHEC") thickeners.

In the present invention at least some of the pigment particles bearing the water-soluble polymer have disposed thereon a plurality of water-insoluble polymer particles; this is the structure referred to herein as a "composite particle". The water-insoluble polymer particles are typically prepared by emulsion polymerization in an aqueous medium. The average particle diameter of such emulsion polymer particles is typically from 40 nm to 1000 nm, preferably from 40 nm to 500 nm, more preferably from 60 nm to 300 nm. Particle sizes herein are those measured by dynamic light scattering on a Brookhaven BI-90 analyzer. The emulsion polymer particles are preferably predominantly anionically stabilized and include anionic or nonionic, or both, surfactant. The emulsion polymer particles may be monodisperse or polydisperse or bimodal with respect to particle size, and may consist of one or more different types, compositions, and particle sizes. The emulsion polymer glass transition temperature ("$T_g$"), herein is that calculated by the Fox equation [*Bulletin of the American Physical Society* 1, page 123 (1956)] and may range from −20° C. to 60° C. and may in some embodiments consist of blends of particles of different $T_g$s, in which case the overall polymer composition is used herein in calculating the $T_g$. The emulsion polymer particles may optionally contain crosslinker that may be uniform, staged, or employed in seed particles. Examples of suitable emulsion polymer compositions include polymers, named for their predominant monomer constitution, include acrylic-, vinyl-acrylic-, styrene-acrylic, vinyl acetate/ethylene-, urethane-, melamine-, epoxy-, alkyd-, acrylonitrile-, styrene-, polybutadiene-, polyisoprene-, ethylene-propylene-, polyvinyl alcohol-, vinyl chloride-, vinylidene chloride-, epoxy-based homopolymers and copolymers, and blends of such compositions. The polymer particles are present in the composite particles at levels ranging from 5 to 50% by weight, based on the total dry weight of the composite particles.

In the method for forming the stable aqueous dispersion including composite particles a pigment particle is dispersed in an aqueous medium in the presence of from 0.1% to 20%, preferably from 0.20% to 10%, more preferably from 0.25% to 5%, and most preferably from 0.3% to 2%, by weight based on the weight of pigment, of a water-soluble polymer, the water-soluble polymer including, as copolymerized units, from 10% to 30%, by weight based on the weight of the water-soluble polymer, ethylenically unsaturated carboxylic acid monomer when the ethylenically unsaturated carboxylic acid monomer has a molecular weight of from 70 to 100 or from 15% to 40%, by weight based on the weight of the water-soluble polymer, ethylenically unsaturated carboxylic acid monomer when the ethylenically unsaturated carboxylic acid monomer has a molecular weight of from greater than 100 to 500; and from 5% to 95%, by weight based on the weight of the water-soluble polymer, ethylenically unsaturated N-containing monomer selected from monomers consisting of monomers having Structure I-IV, and mixtures thereof, wherein the molar ratio of carboxylic acid to N-functionality is from 0.1 to 4; and wherein the calculated $M_n$ of the water-soluble polymer is from 1,000 to 25,000; in an amount of the water-soluble polymer to the pigment of from 0.2% to 5% on a dry weight/dry weight basis; and contacting the dispersed pigment particle with an aqueous dispersion of water-insoluble polymer particles in a ratio of the polymer particles to the pigment particles of from 0.04 to 4.0 dry weight/dry weight basis. The dispersion step may be affected by any means commonly used to disperse pigments in an aqueous medium, including, for example, grinding with a high speed dispersator, or grinding in media mills or ball mills In any event the pigment dispersion must have sufficient stability during storage (substantially maintaining the same particle size with no or minimal sediment formation) and must have sufficient stability to withstand aggregation and coagulation during the subsequent step of contacting the dispersed pigment particle with an aqueous dispersion of polymer particles.

The dispersed pigment particles are contacted with an aqueous dispersion of polymer particles water-insoluble polymer particles in an amount of from 5 to 300% by weight, based on the weight of the composite particles. This step is typically conducted with low shear mixing, preferably for a period of less than 30 minutes at a temperature of the aqueous dispersion of from 5° C. to 50° C.

In one aspect of the present invention a dry coating is formed by the method including: (a) forming an aqueous coating composition including the stable aqueous dispersion including composite particles of the invention; (b) applying the aqueous coating composition to a substrate; and (c) drying, or allowing to dry, the aqueous coating composition. The aqueous coating composition herein expressly includes compositions known in the art as architectural, maintenance, and industrial coatings, caulks, sealants, and adhesives. Aqueous coating compositions include, for example, paint formulations, automotive coatings formulations, architectural and industrial coatings formulations, caulks and sealants, adhesives, inks, paper coatings; coatings and saturants for textiles and nonwovens; adhesives; powder coatings; and traffic paints such as those paints used to mark roads, pavements, and runways. The aqueous coating composition also includes compositions such as, for example, cosmetic formulations, dentifrices, and hand lotions that are not used to form dry coatings of the invention. The aqueous coating composition is typically applied to a substrate such as, for example, wood, metal, plastic, paper and board, leather, marine and civil engineering substrates, cementitious substrates such as, for example, concrete, stucco, and mortar, previously painted or primed surfaces, and weathered surfaces. The aqueous coating composition may be applied to a substrate using conventional coatings application methods such as, for example, brush, roller, caulking applicator, roll coating, gravure roll, curtain coater and spraying methods such as, for example, air-atomized spray, air-assisted spray, airless spray, high volume low pressure spray, and air-assisted airless spray. Drying of the aqueous coating composition to provide a dry coating may be allowed to proceed under ambient conditions such as, for example, at from 5° C. to 35° C. or the coating may be dried at elevated temperatures such as, for example, from 35° C. to 150° C.

The aqueous coating composition including the composite particles may also include one or more of pigment particles not incorporated in composite particles and polymer particles, the same as or different from the polymer particles incorporated into the composite particles. The aqueous coating composition of the present invention optionally additionally includes other materials commonly found in coatings such as opaque polymer particles, such as, for example, extenders, other polymers, hollow sphere, when dry, pigments such as Ropaque™ Opaque Polymers (Dow Chemical Co.), solvents, coalescents at a level of from 0 to 40 wt %, based on the weight of polymer solids, wetting agents, defoamers, rheology modifiers, crosslinkers, dyes, pearlescents, adhesion promoters, dispersants, leveling agents, optical brighteners, ultraviolet stabilizers, preservatives, biocides, and antioxidants.

The examples that follow illustrate aspects of the present invention. The abbreviation "g" represents "grams".

ABBREVIATIONS

BMA=Butyl methacrylate
MMA=Methyl methacrylate
BzMA=Benzyl methacrylate
HEMA=Hydroxyethyl methacrylate
DMAEMA=2-(Dimethylamino)ethyl methacrylate
MAA=Glacial methacrylic acid
DI water=Deionized water

TEST METHODS

Stable Aqueous Compositions

Samples of the aqueous compositions were made, divided, and filled into 250 ml containers. Viscosity was measured at 25° C. with a BYK KU-2 Stormer type viscometer (BYK-Gardner GmbH, Lausitzer Strasse 8, 82538 Geretsried, Germany, Tel +49 8171 3493-0) and measurements made according to ASTM D562. Initial measurements were made within 2 hr of batch completion; 1-day measurements were made after equilibrating the samples at 25° C. for 1 day; 10-day measurements were made after equilibrating the samples at 25° C. for 10 days; and heat age measurements were made after storing the samples at 60° C. for 10 days followed by adjustment to 25° C. for measurement. The final value of viscosity rise, ΔKU, is given by the difference between the heat age measurement, and the initial measured viscosity. "Stable aqueous dispersions" herein are those that have ΔKU less than 10 KU.

Polymer Water Solubility:

"Water solubility" herein refers to a polymer forming a clear solution in water at pH ~8 at 25° C. at greater than 10% w/w, preferably at greater than 20% w/w, and most preferably at greater than 30% w/w.

Kubelka-Munk S/Mil Test Method

Two draw-downs were prepared on Black Release Charts (Leneta Form RC-BC) for each paint using a 38-μm Bird draw down bar and the charts allowed to dry overnight. Using a template, 8.3 cm×10.2 cm rectangles were cut out with an X-ACTO knife on each chart. The Y-reflectance was measured using a BYK Gardner 45/0° Reflectomer in each of the scribed areas five times measuring on a diagonal starting at the top of the rectangle and the average Y-reflectance recorded. A thick film draw down was prepared for each paint on Black Vinyl Charts (Leneta Form P121-10N) using a 635-μm block draw down bar, and the charts were allowed to dry overnight. The Y-reflectance was measured in five different areas of the draw down and the average Y-reflectance recorded. Kubelka-Munk hiding value S is given by Equation 1 (assuming the reflectance of the black substrate is zero):

$$S = \frac{R}{X \times (1-R^2)} \times \ln\frac{1-(R_B \times R)}{1-\frac{R_B}{R}} \qquad \text{Equation 1}$$

where X is the average film thickness, R is the average reflectance of the thick film and RB is the average reflectance over black of the thin film. X can be calculated from the weight of the paint film ($W_{pf}$), the density (D) of the dry film; and the film area (A). Film area for the 8.3 cm×10.2 cm template is 85 cm².

$$X(\mu m) = \frac{W_{pf}(g) \times 10000(\mu m/cm)}{D(kg/m^3) \times 0.001((g/cm^3)) \times A(cm^2)}$$

Synthesis of Sample a, a Water Soluble Polymer
Suitable for Use in the Invention. Poly(methacrylic
acid-co-methyl
methacrylate-co-2-(dimethylamino)ethyl
methacrylate: (30/25/45, by wt)

A three-neck flask equipped with a condenser, a magnetic stirring bar, and a thermocouple was charged with a mixture of ethanol (44 ml) and distilled water (4 ml). MAA (6.0 g), MMA (5.0 g), DMAEMA (9.0 g), 2-mercaptoethanol (0.8 g), and 2,2'-azobis(2-methylpropionamidine)dihydrochloride (0.2 g) were added to the flask and dissolved in the ethanol/water mixture. The reaction mixture was heated to 65° C. in an oil bath and the heating source was removed. The reaction was allowed to heat via exotherm. After the exotherm, the reaction was heated to 78° C. for 1.5 hr. 0.1 g of 2,2'-azobis(2-methylpropionamidine)dihydrochloride in 1 ml distilled water was added and the reaction was heated to 85° C. for 30 min. The reaction was cooled to room temperature and the solvent was removed under reduced pressure. The residue was redissolved in water and the pH was adjusted to neutral by the addition of 30% aqueous ammonia solution.

Synthesis of Sample b, a Water-Insoluble Polymer not Suitable for Use in the Invention According to US 20040250735. Synthesis of Poly(BzMA/DMAEMA/BMA/MMA/HEMA/MAA)

A three-neck flask equipped with a condenser, a magnetic stirring bar, and a thermocouple was charged with a mixture of ethanol (88.2 mL)/water (8.7 mL). Benzylmethacrylate (BzMA, 20.4 g), 2-(dimethylamino)ethyl methacrylate (DMAEMA, 2.8 g), butyl methacrylate (BMA, 6.0 g), methyl methacrylate (MMA, 4.0 g), hydroxyethyl methacrylate (HEMA, 2.0 g), methacrylic acid (MAA, 4.8 g), 2-mercaptoethanol (4%, 1.6 g), and VAZO™ 52 (2,2-Azobis(2,4-dimethylvaleronitrile), 1%, 0.4 g) were added to the flask and dissolved in the ethanol/water mixture. The reaction mixture was heated to 65° C. in an oil bath and the heating source was removed. The reaction was allowed to heat via exotherm. After the exotherm, the reaction was heated to 78° C. for 1.5 hr. The initiator chase (0.2 g VAZO™ 52 in distilled water) was added, and the reaction was heated to 85° C. for 30 min. The reaction was cooled to room temperature. Removal of the ethanol under reduced pressure resulted in precipitation of the insoluble polymer, therefore the polymer was used as-is in a solution in ethanol/water. The pH was adjusted to neutral by the addition of NaOH (50% solution) and the solids adjusted to 30% w/w.

were added after the grind was combined with the binder(s). The volume solids (VS) was 35% and the pigment volume concentration (PVC) was 16% $TiO_2$.

TABLE 1.1

| Aqueous composition formation (all amounts in g) | |
|---|---|
| Grind | |
| Water-soluble polymer (50%) | 1.12 |
| Water | 7.93 |
| TI-PURE ™ R-706 | 37.53 |
| Grind Sub-total | 46.58 |
| Water | 5.00 |
| Grind Sub-total | 51.58 |
| TAMOL ™ SG-10M | 111.54 |
| Mixed 5 min; let stand 25 for total 30 minutes | |
| LetDown | 163.12 |
| TEXANOL ™ | 4.28 |
| Water | 29.03 |
| ACRYSOL ™ RM-2020 E | 4.50 |
| ACRYSOL ™ RM-825 | 0.12 |
| TERGITOL ™ 15-S-9 | 0.40 |
| Totals | 201.45 |

TI-PURE ™ and VAZO ™ are trademarks of E. I. DuPont de Nemours and Co.; TAMOL ™, ACRYSOL ™ and TERGITOL ™ are trademarks of The Dow Chemical Co.; TEXANOL ™ is a trademark of Eastman Chemical Co.

TABLE 1.2

Evaluation of dry coatings for hiding efficacy

| | Water-soluble polymer | Calc. $M_n$ | % Carboxylic acid monomer | % N-containing monomer | Mole ratio acid/amine* | Hiding S/mil |
|---|---|---|---|---|---|---|
| Comp A | (80 MAA/20 DMAEMA) | 3000 | 80 | 20 | 7.3 | 4.60 |
| Comp B | 40 MAA/60 DMAEMA | 3100 | 40 | 60 | 1.2 | 5.05 |
| Comp. C | (60 MAA/20 DMAEMA/20 MMA) | 3000 | 60 | 20 | 5.5 | 5.50 |
| Comp D | (60 MAA/40 DMAEMA) | 3100 | 60 | 40 | 2.7 | 5.60 |
| Comp E | (51 BZMA/7 DMAEMA/15 BMA/10 MMA/5 HEMA/12 MAA) per US 20040250735 | 3000 | 12 | 7 | 3.2 | 6.00 |
| Comp F | 40 MAA/40 DMAEMA/20 MMA | 3000 | 40 | 40 | 1.8 | 6.00 |
| Comp G | 40 MAA/20 DMAEMA/40 MMA | 3000 | 40 | 20 | 3.7 | 6.20 |
| Comp H | 20 MAA/20 DMAEMA/60 MMA | 2900 | 20 | 20 | 1.8 | 6.29 |
| Ex. 1 | 20 MAA/60 DMAEMA/20 MMA) | 3000 | 20 | 60 | 0.6 | 7.04 |
| Ex. 2 | 20 MAA/80 DMAEMA | 3000 | 20 | 80 | 0.5 | 7.21 |
| Ex. 3 | 30 MAA/45 DMAEMA/25 MMA | 3000 | 30 | 45 | 1.2 | 7.81 |

*mole ratio acid/amine ignores any other monomers. Compositions given in monomer w/w percent.

EXAMPLES 1-3 AND COMPARATIVE EXAMPLES A-H

Formation of Aqueous Coating Compositions

Stable aqueous coating compositions, Examples 1-3 were made according to the process shown in Table 1.1. The pigment was dispersed with the water-soluble polymer indicated in Table 1.2, and the same or different dispersant was added later to make up the desired total dispersant level. The grind pH was adjusted to 9. Grind and binder were combined and mixed for about 30 min; the volume solids of this stage was made as high as practical. Surfactants and thickeners Examples 1-3 of the present invention containing composite particles exhibit hiding properties superior to those of Comparative Examples A-H.

We claim:

1. A stable aqueous dispersion comprising composite particles, said composite particles comprising:
   a pigment particle, said pigment particle having disposed thereon a water-soluble polymer, said water-soluble polymer comprising, as copolymerized units, from 10% to 30%, by weight based on the weight of said water-soluble polymer, ethylenically unsaturated carboxylic acid monomer when said ethylenically unsaturated carboxylic acid monomer has a molecular weight of from 70 to 100; or from 15% to 40%, by weight based on the weight of said water-soluble polymer, ethylenically unsaturated carboxylic acid monomer when said ethylenically unsaturated carboxylic acid monomer has a molecular weight of from greater than 100 to a molecular weight of 500; and from 5% to 95%, by weight based on the weight of said water-soluble polymer, ethylenically unsaturated N-containing monomer selected from the group consisting of:

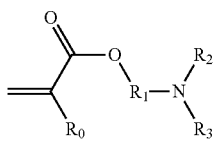

Structure I wherein $R_0$ is H, $CH_3$, or $CH_2CH_3$; $R_1$ is $CH_2CH_2$, $CH_2CH(CH_3)$, or $CH_2CH_2CH_2$, or $CH(CH_3)CH_2CH_2$, $CH_2CH_2CH_2CH_2$, $CH(CH_2CH_3)CH_2$, $CH(CH_3)CH(CH_3)$; $R_2$ and $R_3$ are, independently, H, $CH_3$, $CH_2CH_3$, or $C_3$-$C_{12}$ and selected from the group consisting of: linear, branched, alkyl, aromatic, and cyclic structures; or quaternary ammonium analogues of Structure I;

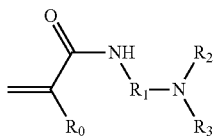

Structure II wherein $R_0$ is H, $CH_3$, $CH_2CH_3$; and $R_1$ is $CH_2CH_2$, $CH_2CH(CH_3)$, or $CH_2CH_2CH_2$; $R_2$ and $R_3$ are, independently, H, $CH_3$, $CH_2CH_3$, or $C_3$-$C_{12}$ selected from the group consisting of: linear: branched, alkyl, aromatic, and cyclic structures; or quaternary ammonium analogues of Structure II;

Structures III - vinyl pyridine

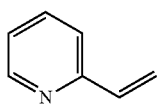

IIIa

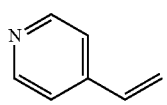

IIIb

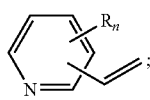

IIIc wherein R is $C_1$-$C_4$ alkyl and n is 0 to 4;

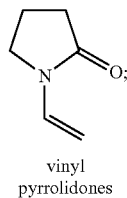

Structure IV vinyl pyrrolidones and mixtures thereof; wherein the molar ratio of carboxylic acid to N-functionality is from 0.1 to 4; and from 0% to 50%, by weight based on the weight of said water-soluble polymer, (meth)acrylic ester of a linear or branched monohydroxyl or amide of a monoamine compound having from 1 to 4 carbon atoms; or vinyl ester of a linear, branched, cyclic, or aromatic monocarboxylic acid having from 1 to 9 carbon atoms; and wherein the calculated $M_n$ of said water-soluble polymer is from 1,000 to 25,000; and said pigment particle bearing said water-soluble polymer having disposed thereon a plurality of water-insoluble polymer particles in an amount of from 5 to 50% by weight, based on the weight of the composite particles.

2. The stable aqueous dispersion of claim 1 wherein said ethylenically unsaturated N-containing monomer is selected from the group consisting of Structure I.

3. The stable aqueous dispersion of claim 1 wherein said pigment particle is an inorganic pigment particle having an average particle diameter of from 0.05 microns to 10 microns.

4. The stable aqueous dispersion of claim 1 wherein said inorganic pigment particle comprises $TiO_2$.

5. The stable aqueous dispersion of claim 1 wherein said ethylenically unsaturated carboxylic acid monomer is (meth)acrylic acid or a salt thereof.

6. The stable aqueous dispersion of claim 1 further comprising at least one thickener selected from the group consisting of: hydrophobically modified ethoxylated urethanes ("HEUR"), hydroxyethyl cellulose ("HEC"), alkalisoluble emulsions ("ASE"), hydrophobically modified alkali-soluble emulsions ("HASE"), and hydrophobically modified hydroxyethyl cellulose ("HMHEC") thickeners.

7. A method for forming a stable aqueous dispersion comprising composite particles comprising:

a) dispersing a pigment particle in an aqueous medium in the presence of from 0.1% to 20%, by weight based on the weight of pigment, of a water-soluble polymer, said water-soluble polymer comprising, as copolymerized units, from 10% to 30%, by weight based on the weight of said water-soluble polymer, ethylenically unsaturated carboxylic acid monomer when said ethylenically unsaturated carboxylic acid monomer has a molecular weight of from 70 to 100; or from 15% to 40%, by weight based on the weight of said water-soluble polymer, ethylenically unsaturated carboxylic acid monomer when said ethylenically unsaturated carboxylic acid monomer has a molecular weight of from greater than 100 to a molecular weight of 500; and from 5% to 95%, by weight based on the weight of said water-soluble polymer, ethylenically unsaturated N-containing monomer having the structure:

Structure I

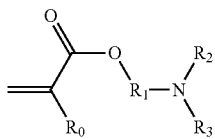

wherein $R_0$ is H, $CH_3$, or $CH_2CH_3$; R1 is $CH_2CH_2$, $CH_2CH(CH_3)$, or $CH_2CH_2CH_2$, or $CH(CH_3)CH_2CH_2$, $CH_2CH_2CH_2CH_2$, $CH(CH_2CH_3)CH_2$, $CH(CH_3)CH(CH_3)$; $R_2$ and $R_3$ are, independently, H, $CH_3$, $CH_2CH_3$, or $C_3$-$C_{12}$ selected from the group consisting of: linear, branched, alkyl, aromatic, and cyclic structures; or quaternary ammonium analogues of Structure I;

Structure II

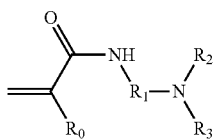

wherein $R_0$ is H, $CH_3$, $CH_2CH_3$; and $R_1$ is $CH_2CH_2$, $CH_2CH(CH_3)$, or $CH_2CH_2CH_2$; $R_2$ and $R_3$ are, independently, H, $CH_3$, $CH_2CH_3$, or $C_3$-$C_{12}$ and may be linear, branched, alkyl, aromatic, or cyclic; or quaternary ammonium analogues of Structure II;

Structures III - vinyl pyridine

IIIa

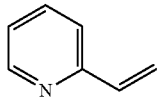

IIIb

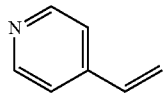

IIIc

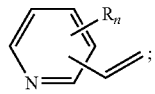

wherein R is $C_1$-$C_4$ alkyl and n is 0 to 4;

Structure IV

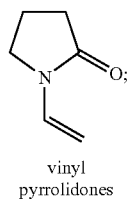

vinyl pyrrolidones and mixtures thereof; wherein the molar ratio of carboxylic acid to N-functionality is from 0.1 to 4; and
from 0% to 50%, by weight based on the weight of said water-soluble polymer, (meth)acrylic ester of a linear or branched monohydroxyl or amide of a monoamine compound having from 1 to 4 carbon atoms; or vinyl ester of a linear, branched, cyclic, or aromatic monocarboxylic acid having from 1 to 9 carbon atoms; and wherein the $M_n$ of said water-soluble polymer is from 1,000 to 25,000; and
(b) contacting said dispersed pigment particle with an aqueous dispersion of water-insoluble polymer particles in an amount of from 5% to 300% by weight, based on the weight of the composite particles.

8. The method of claim 7 wherein said ethylenically unsaturated N-containing monomer is selected from the group consisting of Structure I.

9. The method of claim 7 wherein said contacting step (b) is conducted for a period of less than 30 minutes at a temperature of from 5 to 50° C.

10. A dry coating formed by the method comprising:
a) forming an aqueous coating composition comprising the stable aqueous dispersion comprising composite particles of claim 1;
b) applying said aqueous coating composition to a substrate; and
c) drying, or allowing to dry, said aqueous coating composition.

* * * * *